United States Patent [19]

Savage

[11] Patent Number: 5,552,316
[45] Date of Patent: Sep. 3, 1996

[54] **CLARIFYING *E. COLI* FERMENTATION BROTHS WITH A COMBINATION OF ANIONIC AND CATIONIC FLOCCULANTS**

[75] Inventor: Christopher M. Savage, East Lansing, Mich.

[73] Assignee: Environmental Marketing Services, Ltd., Lansing, Mich.

[21] Appl. No.: 375,002

[22] Filed: Jan. 18, 1995

Related U.S. Application Data

[63] Continuation of Ser. No. 72,542, Jun. 4, 1993, abandoned.

[51] Int. Cl.$^6$ .............................. C12N 1/02; C12P 13/04; B03D 3/00
[52] U.S. Cl. .................. 435/261; 435/106; 435/814; 210/705; 210/723; 210/732
[58] Field of Search .............................. 435/252.2, 814, 435/261, 106; 210/705, 723, 732

[56] References Cited

U.S. PATENT DOCUMENTS

| | | | |
|---|---|---|---|
| Re. 31,900 | 5/1985 | Halverson | 210/734 |
| 3,002,960 | 10/1961 | Kolodny | 260/89.7 |
| 3,316,181 | 4/1967 | Sackis | 252/344 |
| 3,374,143 | 3/1968 | Stephenson | 162/190 |
| 3,686,109 | 8/1972 | Aldrich et al. | 260/29.6 |
| 3,692,673 | 9/1972 | Hoke | 210/52 |
| 4,010,131 | 3/1977 | Phillips et al. | 260/29.4 |
| 4,147,681 | 4/1979 | Lim et al. | 260/29.6 |
| 4,251,651 | 2/1981 | Kawakami et al. | 526/204 |
| 4,392,917 | 7/1983 | Lipowski et al. | 162/168.1 |
| 4,396,752 | 8/1983 | Cabestany et al. | 526/287 |
| 4,451,628 | 5/1984 | Dammann | 526/225 |
| 4,565,635 | 1/1986 | Le Du et al. | 210/727 |
| 4,693,830 | 9/1987 | Thornton et al. | 210/734 |
| 4,695,453 | 9/1987 | Tuominen et al. | 424/81 |
| 4,702,844 | 10/1987 | Flesher et al. | 210/733 |
| 4,770,803 | 9/1988 | Forsberg | 252/75 |

*Primary Examiner*—David M. Naff
*Assistant Examiner*—Francisco C. Prats
*Attorney, Agent, or Firm*—Alfred D. Lobo

[57] ABSTRACT

A method which uses a combination of polymeric cationic and an anionic flocculants to clarify an aqueous solution containing cells of a microorganism and parts thereof is described. The anionic flocculant is based upon a copolymer of an alpha-beta unsaturated monomer of an anhydride, a carboxylic acid or salt and an alpha-beta Unsaturated sulfonic acid or salt monomer. The polymeric cationic surfactant is preferably a quaternary ammonium or tertiary amine containing polymer produced from an alpha-beta unsaturated amino monomer. The method is particularly useful for clarifying solutions wherein a bacterium is used to produce an expressed material such as a protein, peptide, or amino acid dissolved in the solution which is to be separated from the cells or cell parts. Particularly preferred is a method wherein the anionic polymer and therafter the cationic polymer are mixed sequentially into the fermentation broth whereby a flocculant mass containing the polymers, cells and parts of cells is allowed to separate from the broth.

17 Claims, 1 Drawing Sheet

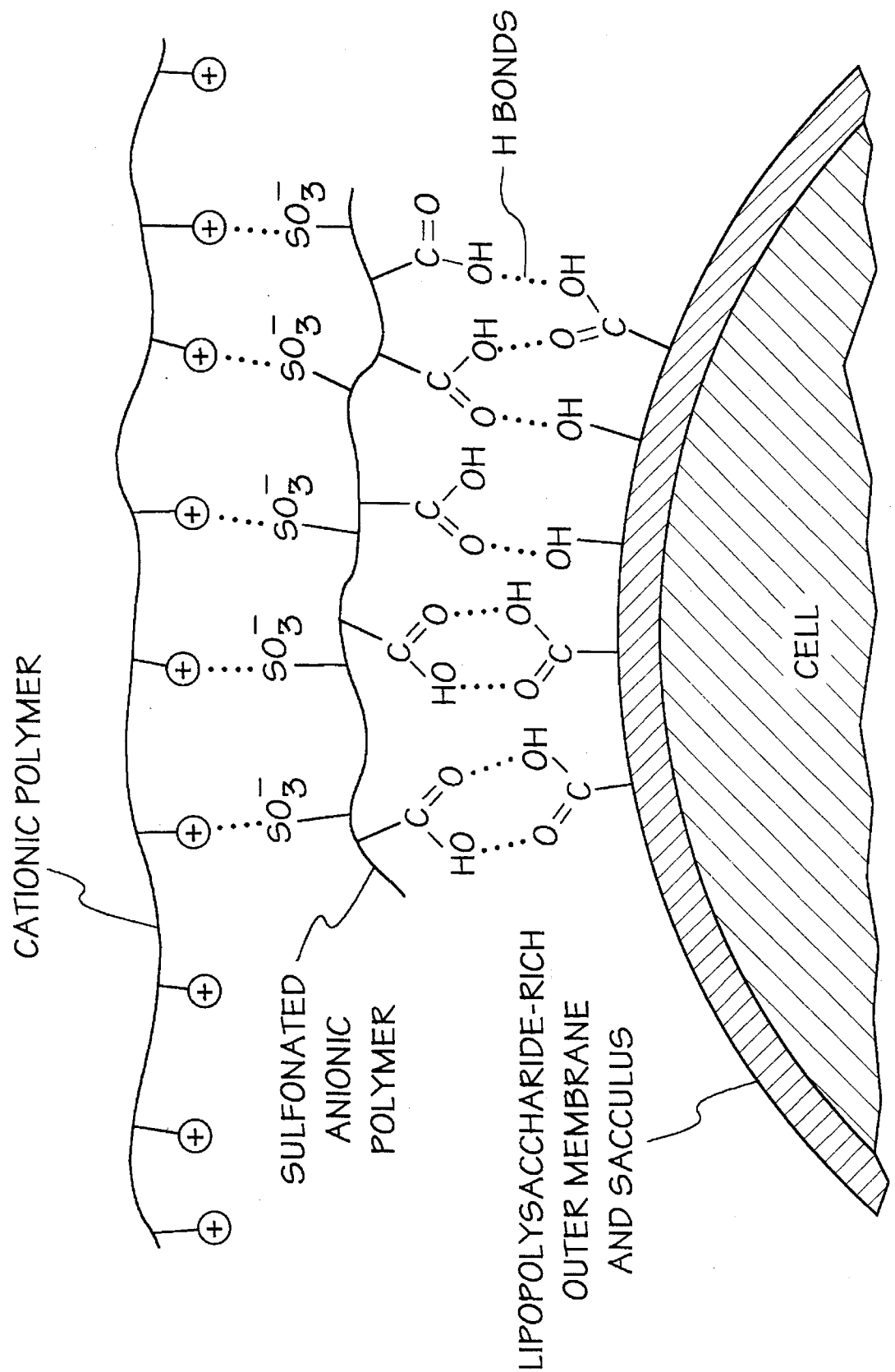

CLARIFYING E. COLI FERMENTATION BROTHS WITH A COMBINATION OF ANIONIC AND CATIONIC FLOCCULANTS

This is a continuation of application Ser. No. 08/072,542 filed on Jun. 4, 1993, now abandoned.

BACKGROUND OF INVENTION (1) Field of the Invention

The present invention relates to a novel method of using differently charged polymers which are flocculants for clarifying aqueous solutions of a microorganism, particularly *Escherichia coli* ("*E. coli*") cells containing recombinant DNA which express a foreign protein. In particular, the present invention relates to a method which uses an anionic and a cationic polymer in sequence to flocculate the cells.

(2) Description of Related Art

Microorganisms in a culture or growth medium are typically extremely difficult to settle, thicken, concentrate and dewater which is referred to as "clarifying" in the industrial setting. The terms "microorganism" here particularly refers to bacteria, fungi and yeasts, which can be living or dead. The term "clarifying" designates dewatering, sedimentation, consolidation, flocculation, thickening, settling, concentrating or other separation activities which result in a clearer aqueous solution.

In order to clarify solutions containing microorganisms, a common procedure is to add cationic (positively charged) flocculants, which are polyelectrolytes, particularly high molecular weight derivatives of polyacrylamide. However, if the microorganism being treated does not contain sufficient surface negative charge, the treatment with cationic polymers is not always successful.

In some instances, the use of cationic polymers is improved with inorganic coagulants such as alum, ferric chloride or other salts. However, these materials can result in a less favorable sludge or floc due to a change in the pH or an increase in the amount of non-biodegradable and non-combustible material in the separated solids making them unattractive for landfilling or incineration. They can also cause increased corrosion to process equipment, can necessitate the handling of additional hazardous materials and can create greater floc volume.

Polymeric anionic and cationic flocculants are disclosed, for instance, in U.S. Pat. Re No. 31,900 to Halverson, U.S. Pat. No. 3,002,960 to Kolodny, U.S. Pat. Nos. 3,316,181 to Sakis, 3,686,109 to Aldrich, U.S. Pat. No. 3,692,673 to Hoke et al, U.S. Pat. No. 3,374,143 to Stephenson, U.S. Pat. No. 4,010,131 to Phillips et al, U.S. Pat. No. 4,451,628 to Damman, U.S. Pat. No. 4,565,635 to Du et al, U.S. Pat. Nos. 4,702,844 to Flesher et al, 4,693,830 to Thorton et al, 4,695,453 to Tuominen et al, U.S. Pat. No. 4,147,681 to Lim et al, and U.S. Pat. No. 4,770,803 to Forsberg. These polymers are derived from alpha-beta unsaturated monomers and the external charge depends on whether the pendent groups are positively (cationic) or negatively (anionic) charged. The problem has been that these flocculants have shown only limited utility in clarifying suspensions of microbial materials.

OBJECTS

It is therefore an object of the present invention to provide a method for clarifying an aqueous solution containing *Escherichia coli* cells and parts of the microorganism. In particular it is an object of the present invention to provide a method which uses a unique combination of polymeric anionic and cationic flocculants in sequence. Further still, it is an object of the present invention to provide a method which is simple and economical. These and other objects will become increasingly apparent by reference to the following description and the drawing.

BRIEF DESCRIPTION OF THE DRAWING

FIG. 1 is a schematic view showing a possible mechanism for the clarifying of solutions containing the *E. coli* cells with the anionic and cationic polymers.

DESCRIPTION OF PREFERRED EMBODIMENTS

The present invention relates to a method for clarifying an aqueous solution containing suspended cells and parts of cells of a microorganism by introducing a flocculating composition, the improvement which comprises:

(a) sequentially mixing an anionic polymer A and a cationic polymer C in the solution, wherein the anionic polymer A contains (i) about 5 to 95 mole percent of repeating units of an alpha-beta unsaturated carboxylic acid or salt monomer selected from the group consisting of an alcohol, anhydride, a carboxylic acid and a salt of the acid wherein the salt is an alkali metal or alkaline earth metal salt and (ii) 5 to 95 mole percent of repeating units of an alpha-beta unsaturated sulfonic acid or salt monomer wherein the salt is an alkali metal or alkaline earth metal salt; and the cationic polymer C contains at least one alpha-beta unsaturated amino monomer, wherein the ratio of A to C is between about 1:1 and 100:1 by weight and the polymers are present in a concentration in the range from 1 ppm (parts per million) to 5000 ppm of the solution;

(b) allowing the flocculants and cells and parts of cells to separate from the solution; and (c) removing the cells and parts of cells and flocculants from the solution.

The method of the present invention overcomes the problem of clarifying aqueous solutions containing *E. coli* cells which have expressed a product such as a peptide, protein, amino acid or pharmaceutical product in solution. The method results in a clearer supernate in the settling operations, a better separation in concentrating applications and a drier sludge cake in dewatering operations. Surprisingly, addition of the anionic polymer A, first, lowers the amount of cationic polymer C which is then necessary to accomplish the clarification.

The anionic flocculants used are water-soluble, anionic polyelectrolyte polymers prepared from at least one monomer selected from each of the following two groups: (1) an $\alpha,\beta$-unsaturated monomer which in solution forms hydrogen bonds with the *E. coli* cells and (2) an $\alpha,\beta$-unsaturated monomer containing a sulfonic acid group or its salt. Other monomers may be used to alter the molecular weight or configuration but at least one of each of these specified monomers should be present. Monomers capable of forming hydrogen bonds when polymerized include, but are not limited to, acrylic acid, maleic acid, methacrylic acid, vinyl alcohol, maleic anhydride and methylol acrylamide.

Monomers containing a sulfonic acid group or its alkali metal, alkaline earth metal or ammonium salt include, but are not limited to, allyl sulfonic acid, methallyl sulfonic acid, allyl ether sulfonic acid, styrene sulfonic acid, methyl styrene sulfonic acid, vinyl sulfonic acid, 2-sulfoxy ethyl methacrylate, or 2-acrylamido-2-methylpropane sulfonic acid, or their sodium, potassium, calcium, ammonium or other alkaline earth metal salts.

Other monomers which may be utilized to modify the structure or molecular weight of the anionic flocculant include, but are not limited to acrylamide, methylenebisacrylamide, or monomers capable of copolymerizing with the previously disclosed monomers a disclosed in the prior art. These monomers should be present in amounts which do not render the polymer water insoluble. The weight ratio of the hydrogen bond forming monomer (1) to the sulfonic acid containing monomer (2) can be from 5:95 to 95:5.

The molecular weight of the resulting anionic polymers can vary widely from one thousand to several millions. In fact, blends or mixtures of high molecular weight anionic polymers with lower molecular weight anionic polymers can be very effective. Thus blending polymers which differ in charge density and molecular weight is within the scope of this invention. The viscosity of the anionic flocculant is preferably between about 10 and 1 million CPS, Brookfield viscosity, Spindle No. 4 at 15% by weight solids in water.

The cationic polymers have positively charged pendent lower alkyl groups. The lower alkyl groups may contain from 1 to 10 carbon atoms which can be straight chain or branched groups such as trimethyl ammonium groups or tertiary amine groups. The tertiary amine groups can quaternize under acid conditions below pH 7 as is well known to those skilled in the art. The viscosity is preferably between about 500 and 100,000 CPS Brookfield viscosity, spindle no. 4 at 1% by weight solids. The molecular weight is preferably between 1 million and 30 million.

In the cationic polymer, preferably between about 10 and 99 mole percent of a cationic group forming monomer is used with the balance being acrylamide. Preferably the cationic monomer is quaternized.

The polymers of this invention are prepared by any of the typical polymerization methods known to those skilled in the art as discussed previously. These include, but are not limited to, free-radical polymerization, radiation induced polymerization, solution polymerization, inverse emulsion or microemulsion polymerization or solid-state polymerization or combinations thereof.

The solutions preferably contain between about 1 and 25 volume percent of the cells and cell parts and have a pH between about 2 and 10. The polymers are stirred into the solution, preferably at 10 to 300 rpm using a paddle type stirrer. Filter aids can be used, such as cellulosic materials and clays. Sodium bentonite as the clay or cellulose fibers as the cellulosic materials are preferred. The filter aids are preferably added with the anionic polymer.

Although the mechanism for the improved results of the method of the present invention is not completely understood, it is thought to be as follows: the hydrogen bond forming portion of the anionic polymer hydrogen bonds with the carboxylic acid and hydroxyl groups in the protective coating of the cell wall of the microorganism. The sulfonic acid groups on the anionic polymer provide reactive anchoring points for the cationic polymer, while the anionic polymer attaches to the microorganism thus allowing the anionic and cationic polymers to be more effective. In other words, the cationic polymer binds to the anionic polymer after the anionic polymer has bonded to the cell wall of the microorganism. FIG. 1 shows the mechanism schematically. Sulfonic acid groups are important since many aqueous fermentation broths containing the microorganisms to be flocculated are high in dissolved salts and may have low pHs (pH 1 to 5). The sulfonic acid groups are resistant to low pH conditions and retain their negative charge. Carboxyl groups and polymers derived from carboxylic acids, such as acrylic acid, lose their negative charge under low pH conditions and become ineffective.

With some strains of *E. coli*, the amount of the cationic polymer which, if used alone, produces substantial flocculation, or which might satisfactorily flocculate the cells is reduced by the addition of the anionic polymer. Since the use of the anionic polymer is not increasing the demand for the cationic flocculant as would be expected, it would appear that the anionic flocculant is increasing the effectiveness of the cationic flocculant; that is, they are better anchored to the solids so less is required.

The effectiveness of the combination of anionic and cationic polymers as a flocculant is particularly evidenced in settling of *E. coli* cells in fermentation processes which produce the aforementioned product expressed by the cells. The culture or grouwth media are typically very high in dissolved salts. Also, the *E. coli* utilized are often genetically engineered with recombinant DNA to make them more productive. This increase in productivity is often coupled with a decrease in the formed mass of the protective outer membrane and sacculus of the cell wall. This coating carries a very slight surface negative charge due to the hydroxyl and carboxyl groups in the lipopolysaccharide-rich outer membrane thereby allowing the cationic flocculants to clarify aqueous solutions of the bacteria. However, when there is a decrease in the formed mass of this coating, as happens with these genetically-engineered bacteria, there is less negative charge than the original non-engineered bacteria, so that the cationic flocculant can form an electrostatic bond only with great difficulty. Unexpectedly the use of the anionic flocculants as in the method of this invention provides the additional charge needed to flocculate and settle the cells with the cationic flocculant.

EXAMPLE 1

The tests in Example 1 show the effect of sequential addition of the sulfonated anionic polymer and the cationic polymer as evidenced by the size of the floc and clarity even at relatively low concentrations of the cationic polymer in the broth. The comparison polymer did not affect these parameters.

A fermentation broth in which an amino acid is expressed from a recombinant strain of *E. coli* present in a concentration of about 6% by weight of the broth is used in each of the tests tabulated. The appearance of the broth was an opaque, tan dispersion which settled on its own into 2 layers, each about 50% by volume in a settling period in the range from about 3 to 4 hours. The pH of the broth was 2.7. The object of this Example was to compare the effectiveness of the several tests to separate the bacterial cells, which were essentially dead, to produce a supernate from which the recovery af the amino acid is facilitated. The amino acid is recovered by subsequent crystallization steps which remove the amino acid from the solution.

One (1) liter of broth was placed on a gang-stirrer, which is a mixer equipped with multiple ¾"×1 ¾" (1.9 cm×4.4 cm) paddles. In each test, the broth was mixed with the anionic flocculant identified in Table 1 for one (1) minute at high speed. The anionic polymer was added as a 5% by weight solution. Thereafter, the stated dosage of a high molecular weight and high charge density cationic polyacrylamide copolymer (acrylamide 20 mole percent and dimethylamino ethyl acrylate quaternized with methyl chloride) was added to flocculate the suspension. The molecular weight of the flocculant was 5 million. The cationic polymer was added as a 0.25% by weight solution. Once the cationic polymer was added, it was mixed on high speed for 30 seconds and then the mixing was stopped. (The percentages of the diluted polymers are expressed by weight in the tests). In each test the percentage of settled cell material was measured after an additional three (3) minutes and the clarity of the resultant supernatant liquid was measured visually as indicated. The results are shown in Table 1.

TABLE 1

| Anionic Additive | Conc. of anionic | Conc. of cationic | Floc size | Clarity of supernate |
|---|---|---|---|---|
| Control | None | 50 mg/L | 5 | 5 |
| Control | None | 90 mg/L | 5 | 5 |
| Comparison polymer | 1500 mg/L | 90 mg/L | 5 | 5 |
| Polymer 1 | 750 mg/L | 70 mg/L | 6 | 7 |
| Polymer 1 | 1000 mg/L | 70 mg/L | 6 | 7 |
| Polymer 2 | 400 mg/L | 70 mg/L | 8 | 10 |
| Polymer 2 | 800 mg/L | 70 mg/L | 9 | 10 |
| Polymer 3 | 400 mg/L | 80 mg/L | 10 | 10 |
| Polymer 3 | 1600 mg/L | 80 mg/L | 10 | 10 |
| Polymer 4 | 400 mg/L | 50 mg/L | 10 | 10 |
| Polymer 4 | 800 mg/L | 50 mg/L | 10 | 10 |
| Polymer 5 | 400 mg/L | 50 mg/L | 10 | 10 |
| Polymer 5 | 800 mg/L | 50 mg/L | 10 | 10 |
| Polymer 5 | 1600 mg/L | 50 mg/L | 10 | 10 |

Notes:
Floc size rating: 1 = No visible flocculation. 10 = Large, fast settling, sturdy flocs formed.
Clarity rating: 1 = No visible separation within 2 minutes. 10 = Crystal clear, no visible fines or turbidity.

Comparison Polymer: Copolymer of sodium acrylate (30 mole %) and acrylamide, molecular weight approximately 5 million. The polymer does not contain sulfonic acid or sulfonate salt groups. This product is a standard flocculant used in solids separation (Sanyo, Japan, SanFloc AH 330P).

Polymer 1: Blend of (i) a low molecular weight copolymer of sodium allylsulfonate (30 mole %) and sodium acrylate (polymer A1) with (ii) a high molecular weight terpolymer of sodium allylsulfonate (10 mole %), acrylamide (20 mole %) and sodium acrylate (polymer A2). Polymer A1 has a Brookfield viscosity 800 cps (spindle #4, 6 rpm) at 25% solids (the percentages of the solids in the tests are expressed by weight). Polymer A2 has a Brookfield viscosity of 80,000 cps at 15% solids. The blend ratio is 25% of polymer A1 and 75% of polymer A2 by weight.

Polymer 2: Copolymer of sodium 2-acrylamido-2-methylpropanesulfonate (13 mole %) and sodium acrylate. This polymer has a Brookfield viscosity of 40,000 cps at 15% solids.

Polymer 3: Terpolymer of sodium allylsulfonate (15 mole %), acrylamide (70 mole %) and sodium acrylate. It has a Brookfield viscosity of 50,000 cps at 15% solids.

Polymer 4: Same as Polymer 2, Brookfield viscosity of 30,000 cps.

Polymer 5: Same as Polymer 2, Brookfield viscosity of 10,000 cps.

EXAMPLE 2

Example 2 shows that the sequential addition of the sulfonated anionic polymers with the cationic polymers of this invention generate a more easily dewatered sludge than the control, both with and without the comparison polymer. No sludge cake was formed without the inclusion of the sulfonated polymer.

A slurry of bacterial cells from the recombinant strain of *E. coli* was used. The slurry resulted from Example 1 with clean water added. The concentration of cells in the slurry was 12% (w/w) and the slurry had a pH in the range from 2 to 3. The object was to dewater the slurry as much as possible. The drier the sludge cake, the more beneficial the process in removing residual amino acid and in waste management.

Five hundred (500) mL of cell slurry was placed into a 1 liter beaker. A filter aid (sodium bentonite clay or cellulose fibers) was added at 10,000 mg/L and anionic polymer set forth in Table 2 and the slurry was poured between two beakers for a total of 10 times. Cationic polymer was added and poured back and forth for an additional 10 times. The resulting mixture was poured into a laboratory basket centrifuge with a fabric strip for collection of the sludge cake. The percent solids of the cake (if any) and the turbidity of the filtrate were observed and recorded. Anionic flocculant was added as a 10% solution and the cationic polymer was added as a 0.5% solution. The cationic polymer was the copolymer of acrylamide (20 mole %) and dimethylaminoethyl acrylate quaternized with methyl chloride of Example 1. The molecular weight of the cationic polymer was approximately 5 million. The results are set forth in Table 2.

TABLE 2

| Anionic Additive | Conc. of anionic additive | Filter aid type | Conc. of cationic | Turbidity of filtrate | % solids of cake |
|---|---|---|---|---|---|
| Control | None | Clay | 100 mg/L | 1 | No cake |
| Comparison polymer | 500 mg/L | Clay | 100 mg/L | 1 | No cake |
| Comparison polymer | 1000 mg/L | Clay | 50 mg/L | 1 | No cake |
| Comparison polymer | 1000 mg/L | Clay | 100 mg/L | 1 | No cake |
| Comparison polymer | 1000 mg/L | Cellulose | 100 mg/L | 1 | No cake |
| Polymer 6 | 500 mg/L | Clay | 50 mg/L | 7 | 35% |
| Polymer 6 | 1000 mg/L | Clay | 50 mg/L | 8 | 39% |
| Polymer 6 | 1000 mg/L | Clay | 100 mg/L | 9 | 43% |
| Polymer 6 | 1000 mg/L | Cellulose | 50 mg/L | 9 | 44% |
| Polymer 2 | 500 mg/L | Clay | 50 mg/L | 9 | 42% |
| Polymer 2 | 1000 mg/L | Clay | 50 mg/L | 9 | 43% |
| Polymer 2 | 1000 mg/L | Cellulose | 50 mg/L | 10 | 46% |
| Polymer 2 | 1000 mg/L | Cellulose | 100 mg/L | 10 | 46% |

Notes:
Turbidity rating: 1 = Opaque, complete breakdown of flocs. 10 = Clear free from fines and turbidity.

Comparison Polymer: As in Example 1, copolymer of sodium acrylate (30 mole %) and acrylamide, molecular weight approximately 5 million. This product is a standard flocculant used in solids separation.

Polymer 6: Copolymer of sodium allylsulfonate (10 mole %), acrylamide (20 mole %) and sodium acrylate. This polymer is 15% active and has a Brookfield viscosity (Spindle #4, 6 rpm) of 6,500 cps at 15 percent solids.

Polymer 2: Copolymer of sodium 2-acrylamido-2-methyl-propanesulfonate (13 mole %) and sodium acrylate. This polymer has a Brookfield viscosity of 40,000 cps at 15% actives.

EXAMPLE 3

Example 3 shows that the anionic sulfonated polymers followed by the cationic polymers give superior settling of non-genetically modified organisms at lower concentrations of the cationic polymer and give improved clarity of the supernate. The sulfonated polymers showed an improvement when used in the range of 50 to 2000 mg/L (or ppm) in a 15% solution when the cationic Polymer 10 was in the range of 50 to 70 mg/L (or ppm). All of the sulfonated polymers improved the settling rate or clarity when the cationic polymer was used at 50 mg/L (or ppm) which demonstrates that the use of the polymers of this invention can reduce the concentration of the cationic polymer needed to accomplish the clarification. The comparison polymer showed no improvement.

A fermentation broth from the production of an amino acid via a non-genetically modified strain of E. coli was used. The approximate level of bacterial cells was 6%. The appearance of the broth was an opaque, tan dispersion which settled on its own into 2 layers, each about 40% by volume in a settling period in the range from 8 to 10 hours. The pH of the broth was 3.2. The broth contained approximately 35 grams per liter of the amino acid. The object was to separate the dead bacterial cells from the supernate to facilitate the recovery of the amino acid in subsequent crystallization steps. The clearer the supernate, the more beneficial the separation steps from removing the amino acid from the solution. Five hundred (500) mL of broth was placed on a gang-stirrer equipped with ¾"×1¾" paddles. The broth was mixed with the anionic polymer for one (1) minute at 200 to 300 rpm. A dosage of high molecular weight and high charge density cationic derivative of polyacrylamide was then added to flocculate the suspension. Once the cationic polymer was added it was mixed at 200 to 300 rpm for 60 seconds and then the agitation was stopped. The percentage of settled cell material was measured after an additional three (3) minutes and the turbidity of the resulting supernate was measured using a turbidimeter. The anionic polymer was added as a 5% dilution and the cationic polymer is added as a 0.25% dilution. The results are shown in Table 3.

RESULTS FOR EXAMPLE 3

| Anionic additive | Conc. of anionic | Cationic additive | Conc. of cationic | % Settled after 3 mins. | Turbidity of supernate |
| --- | --- | --- | --- | --- | --- |
| None | 0 | None | 0 | 0 | opaque |
| None | 0 | Polymer 10 | 5 mg/L | 0 | opaque |
| None | 0 | Polymer 10 | 25 mg/L | 0 | opaque |
| None | 0 | Polymer 10 | 50 mg/L | 54% | 16 NTU |
| None | 0 | Polymer 10 | 70 mg/L | 59% | 21 NTU |
| None | 0 | Polymer 10 | 90 mg/L | 50% | 20 NTU |
| None | 0 | Polymer 10 | 120 mg/L | 51% | 32 NTU |
| None | 0 | Polymer 10 | 200 mg/L | 52% | 67 NTU |
| None | 0 | Polymer 11 | 50 mg/L | 0 | OPAQUE |
| None | 0 | Polymer 11 | 100 mg/L | 47% | 35 NTU |
| None | 0 | Polymer 11 | 200 mg/L | 54% | 32.5 NTU |
| Polymer 2 | 400 mg L | None | 0 | 0% | Opaque |
| Polymer 2 | 800 mg/L | None | 0 | 0% | Opaque |
| Polymer 2 | 1600 mg/L | None | 0 | 0% | Opaque |
| Polymer 2 | 50 mg/L | Polymer 10 | 50 mg/L | 54% | 12 NTU |
| Polymer 2 | 50 mg/L | Polymer 10 | 70 mg/L | 49% | 12 NTU |
| Polymer 2 | 50 mg/L | Polymer 10 | 100 mg/L | 51% | 17 NTU |
| Polymer 2 | 50 mg/L | Polymer 10 | 200 mg/L | 54% | 45 NTU |
| Polymer 2 | 200 mg L | Polymer 10 | 50 mg/L | 45% | 13 NTU |
| Polymer 2 | 200 mg/L | Polymer 10 | 70 mg/L | 54% | 15 NTU |
| Polymer 2 | 400 mg/L | Polymer 10 | 50 mg/L | 54% | 14 NTU |
| Polymer 2 | 400 mg/L | Polymer 10 | 70 mg/L | 51% | 15 NTU |
| Polymer 2 | 800 mg/L | Polymer 10 | 50 mg/L | 50% | 12 NTU |
| Polymer 2 | 800 mg/L | Polymer 10 | 70 mg/L | 52% | 18 NTU |
| Polymer 2 | 2000 mg/L | Polymer 10 | 10 mg/L | 0.5% | OPAQUE |
| Polymer 2 | 2000 mg/L | Polymer 10 | 25 mg/L | 14% | 51 NTU |
| Polymer 2 | 2000 mg/L | Polymer 10 | 50 mg/L | 53% | 12 NTU |
| Polymer 2 | 2000 mg/L | Polymer 10 | 70 mg/L | 50% | 15 NTU |
| Polymer 2 | 400 mg/L | Polymer 11 | 50 mg/L | 3% | OPAQUE |
| Polymer 2 | 400 mg/L | Polymer 11 | 100 mg/L | 57% | 17 NTU |
| Polymer 2 | 400 mg/L | Polymer 11 | 200 mg/L | 54% | 25 NTU |
| Polymer 2 | 800 mg/L | Polymer 11 | 50 mg/L | 25% | 20 NTU |
| Polymer 2 | 800 mg/L | Polymer 11 | 100 mg/L | 57% | 16 NTU |
| Polymer 2 | 800 mg/L | Polymer 11 | 200 mg/L | 58% | 25 NTU |
| Comp. Polymer | 400 mg/L | none | 0 | 0% | OPAQUE |
| Comp. Polymer | 800 mg/L | none | 0 | 0% | OPAQUE |
| Comp. Polymer | 400 mg/L | Polymer 10 | 50 mg/L | <0.5% | OPAQUE |
| Comp. Polymer | 400 mg/L | Polymer 10 | 120 mg/L | 40% | 65 NTU |
| Polymer 1 | 400 mg/L | none | 0 | 0% | OPAQUE |
| Polymer 1 | 800 mg/L | none | 0 | 0% | OPAQUE |
| Polymer 1 | 1600 mg/L | none | 0 | 0% | OPAQUE |
| Polymer 1 | 400 mg/L | Polymer 10 | 50 mg/L | 46% | 16 NTU |
| Polymer 1 | 400 mg/L | Polymer 10 | 120 mg/L | 34% | 23 NTU |
| Polymer 1 | 1600 mg/L | Polymer 10 | 50 mg/L | 50% | 17 NTU |

-continued

RESULTS FOR EXAMPLE 3

| Anionic additive | Conc. of anionic | Cationic additive | Conc. of cationic | % Settled after 3 mins. | Turbidity of supernate |
| --- | --- | --- | --- | --- | --- |
| Polymer 1 | 1600 mg/L | Polymer 10 | 120 mg/L | 55% | 25 NTU |
| Polymer 7 | 400 mg/L | none | 0 | 0% | OPAQUE |
| Polymer 7 | 800 mg/L | none | 0 | 0% | OPAQUE |
| Polymer 7 | 1600 mg/L | none | 0 | 0% | OPAQUE |
| Polymer 7 | 400 mg/L | Polymer 10 | 50 mg/L | 58% | 23 NTU |
| Polymer 7 | 400 mg/L | Polymer 10 | 120 mg/L | 58% | 29 NTU |
| Polymer 7 | 1600 mg/L | Polymer 10 | 50 mg/L | 56% | 12 NTU |
| Polymer 7 | 1600 mg/L | Polymer 10 | 120 mg/L | 60% | 29 NTU |
| Polymer 8 | 400 mg/L | none | 0 | 0% | OPAQUE |
| Polymer 8 | 800 mg/L | none | 0 | 0% | OPAQUE |
| Polymer 8 | 1600 mg/L | none | 0 | 0% | OPAQUE |
| Polymer 8 | 400 mg/L | Polymer 10 | 50 mg/L | 13% | N/A |
| Polymer 8 | 400 mg/L | Polymer 10 | 120 mg/L | 47% | 36% |
| Polymer 8 | 800 mg/L | Polymer 10 | 50 mg/L | 57% | 13 NTU |
| Polymer 8 | 800 mg/L | Polymer 10 | 120 mg/L | 49% | 24 NTU |
| Polymer 9 | 400 mg/L | None | 0 | 0% | Opaque |
| Polymer 9 | 1600 mg/L | None | 0 | 0% | Opaque |
| Polymer 9 | 400 mg/L | Polymer 10 | 50 mg/L | 7% | N/A |
| Polymer 9 | 1600 mg/L | Polymer 10 | 120 mg/L | 36% | 19 NTU |
| None | 0 | Polymer 12 | 750 mg/L | 0% | Opaque |
| None | 0 | Polymer 12 | 1500 mg/L | 0% | Opaque |
| None | 0 | Polymer 12 | 3000 mg/L | 3% | N/A |
| Polymer 2 | 400 mg/L | Polymer 12 | 1500 mg/L | 2% | N/A |
| Polymer 2 | 400 mg/L | Polymer 12 | 3000 mg/L | 18% | 17 NTU |
| Polymer 2 | 800 mg/L | Polymer 12 | 1500 mg/L | 2% | N/A |
| Polymer 2 | 800 mg/L | Polymer 12 | 3000 mg/L | 27% | 17 NTU |

Notes:
Polymer 2: Same as above, see after Table 1.
Comparison Polymer: Copolymer of sodium acrylate (30 mole %) and acrylamide, molecular weight approximately 5 million. This product is a standard flocculant used in solids separation. It is sold by Sanyo, Japan under the trade name SanFloc AH 330P.
Polymer 1: Same as above, see after Table 1.
Polymer 7: Same copolymer as Polymer 2, but with a Brookfield viscosity of 8,500 cps.
Polymer 8: Copolymer of sodium allylsulfonate (10 mole %), acrylamide (20 mole %) and sodium acrylate. It has a Brookfield viscosity 15,000 cps at 15% solids.
Polymer 9: Copolymer of sulfonated styrene and maleic anhydride, 1 to 1 molar ratio at 25% solids. The molecular weight of this polymer is approximately 15,000. It is sold under the trade name Versa TL-7 by Alco Chemical Co., Chattanooga, Tenn.
Polymer 10: Copolymer of acrylamide (35 mole %) and dimethylaminoethyl acrylate quaternized with methyl chloride. The molecular weight of the cationic polymer is approximately 5 million. It is sold under the trade name SanFloc CH-109P by Sanyo, Japan.
Polymer 11: Copolymer of acrylamide (20 mole %) and dimethylaminoethyl acrylate quaternized with methyl chloride. The molecular weight of the cationic polymer is approximately 5 million.
Polymer 12: Aminomethylolated polyacrylamide (tertiary amine groups) commonly known as a Mannich polymer. It is produced by performing the Mannich reaction on polyacrylamide with formaldehyde and dimethylamine. This polymer is 6% solids with a Brookfield viscosity of 50,000 cps. The molecular weight is estimated to be about 1 million. NTU is Nephelometric Turbidity Unit. The instrument is manufactured by Hach Company, Loveland, CO., Model #2100A. An optimal NTU is less than about 16 NTU.

EXAMPLE 4

Example 4 shows the same results as Example 3 with a genetically modified organism. Here the sulfonated polymers with cationic polymer showed optimal performance in the range of 50 to 2000 mg/L (or ppm) used in a 15% aqueous solution, when the cationic Polymer 10 was used in the range of 50 to 70 mg/L.

The fermentation broth was from production of an amino acid via a genetically modified strain of E. coli as in Example 1. The approximate level of bacteria cells was 6%. The appearance of the broth was an opaque, tan dispersion which settled on its own into 2 layers, each about 40% by volume in a settling period in the range from 8 to 10 hours. The pH of the broth was 2.5. The broth contained approximately 50 grams per liter of the amino acid. The object was to separate the dead bacterial cells from the supernate to facilitate the recovery of the amino acid in subsequent crystallization steps. The clearer the supernate, the more effective the separation steps for removing the amino acid from the solution.

Five hundred (500) mL of broth was place on a gang-stirrer equipped with ¾"×1¾" paddles. The broth was mixed with the anionic polymer for (1) minute at 200 to 300 rpm. A dosage of high molecular weight and high charge density cationic derivative of polyacrylamide was then added to flocculate the suspension. Once the cationic polymer was added it was mixed at 200 to 300 rpm for 60 seconds and then the agitation was stopped. The percentage of settled cell material was measured after an additional three (3) minutes and the turbidity of the resulting supernate was measured using a turbidimeter, rather than using a visual method. The results are shown in Table 4. The anionic polymer was added as a 5% dilution and the cationic polymer was added as a 0.25% dilution

| RESULTS FOR EXAMPLE 4 | | | | | |
|---|---|---|---|---|---|
| Anionic additive | Conc. of anionic | Cationic additive | Conc. of cationic | % Settled after 3 mins. | Turbidity of supernate |
| None | 0 | None | 0 | 0 | opaque |
| None | 0 | Polymer 10 | 5 mg/L | 0 | opaque |
| None | 0 | Polymer 10 | 25 mg/L | 0 | opaque |
| None | 0 | Polymer 10 | 50 mg/L | 2% | N/A |
| None | 0 | Polymer 10 | 70 mg/L | 50% | 415 NTU |
| None | 0 | Polymer 10 | 90 mg/L | 48% | 410 NTU |
| None | 0 | Polymer 10 | 120 mg/L | 48% | 415 NTU |
| None | 0 | Polymer 10 | 200 mg/L | 45% | 425 NTU |
| Polymer 2 | 400 mg/L | None | 0 | 0.5% | N/A |
| Polymer 2 | 800 mg/L | None | 0 | 1% | N/A |
| Polymer 2 | 1600 mg/L | None | 0 | 2% | N/A |
| Polymer 2 | 50 mg/L | Polymer 10 | 50 mg/L | 5% | N/A |
| Polymer 2 | 50 mg/L | Polymer 10 | 70 mg/L | 50% | 350 NTU |
| Polymer 2 | 50 mg/L | Polymer 10 | 100 mg/L | 45% | 375 NTU |
| Polymer 2 | 50 mg/L | Polymer 10 | 200 mg/L | 35% | 350 NTU |
| Polymer 2 | 200 mg/L | Polymer 10 | 50 mg/L | 50% | 350 NTU |
| Polymer 2 | 200 mg/L | Polymer 10 | 70 mg/L | 45% | 400 NTU |
| Polymer 2 | 400 mg/L | Polymer 10 | 50 mg/L | 50% | 350 NTU |
| Polymer 2 | 400 mg/L | Polymer 10 | 70 mg/L | 50% | 375 NTU |
| Polymer 2 | 800 mg/L | Polymer 10 | 50 mg/L | 45% | 415 NTU |
| Polymer 2 | 800 mg/L | Polymer 10 | 70 mg/L | 40% | 425 NTU |
| Polymer 2 | 2000 mg/L | Polymer 10 | 10 mg/L | 20% | 450 NTU |
| Polymer 2 | 2000 mg/L | Polymer 10 | 25 mg/L | 50% | 400 NTU |
| Polymer 2 | 2000 mg/L | Polymer 10 | 50 mg/L | 40% | 410 NTU |
| Polymer 2 | 2000 mg/L | Polymer 10 | 70 mg/L | 35% | 410 NTU |
| Comp. Polymer | 400 mg/L | none | 0 | 0% | OPAQUE |
| Comp. Polymer | 800 mg/L | none | 0 | 0% | OPAQUE |
| Comp. Polymer | 400 mg/L | Polymer 10 | 50 mg/L | 1% | N/A |
| Comp. Polymer | 400 mg/L | Polymer 10 | 120 mg/L | 33% | 450 NTU |
| Polymer 1 | 400 mg/L | none | 0 | 0% | OPAQUE |
| Polymer 1 | 800 mg/L | none | 0 | 0% | OPAQUE |
| Polymer 1 | 1600 mg/L | none | 0 | 0% | OPAQUE |
| Polymer 1 | 400 mg/L | Polymer 10 | 50 mg/L | 45% | 310 NTU |
| Polymer 1 | 400 mg/L | Polymer 10 | 120 mg/L | 48% | 400 NTU |
| Polymer 1 | 1600 mg/L | Polymer 10 | 50 mg/L | 40% | 350 NTU |
| Polymer 1 | 1600 mg/L | Polymer 10 | 120 mg/L | 48% | 400 NTU |
| Polymer 7 | 400 mg/L | none | 0 | 0% | OPAQUE |
| Polymer 7 | 800 mg/L | none | 0 | 0.5% | N/A |
| Polymer 7 | 1600 mg/L | none | 0 | 0.5% | N/A |
| Polymer 7 | 400 mg/L | Polymer 10 | 50 mg/L | 40% | 410 NTU |
| Polymer 7 | 400 mg/L | Polymer 10 | 120 mg/L | 30% | 400 NTU |
| Polymer 7 | 1600 mg/L | Polymer 10 | 50 mg/L | 35% | 400 NTU |
| Polymer 7 | 1600 mg/L | Polymer 10 | 120 mg/L | 50% | 350 NTU |
| Polymer 8 | 400 mg/L | none | 0 | 0% | OPAQUE |
| Polymer 8 | 800 mg/L | none | 0 | 0% | OPAQUE |
| Polymer 8 | 1600 mg/L | none | 0 | 0% | OPAQUE |
| Polymer 8 | 400 mg/L | Polymer 10 | 50 mg/L | 40% | 375 NTU |
| Polymer 8 | 400 mg/L | Polymer 10 | 120 mg/L | 40% | 400 NTU |
| Polymer 8 | 800 mg/L | Polymer 10 | 50 mg/L | 40% | 350 NTU |

Notes:

The comparison polymer, and polymers 1, 2, 7, 8 and 10 correspond to those similarly identified in the tests reported in Example 3 hereinabove.

EXAMPLE 5

Example 5 demonstrates the ability of the combination of anionic and cationic polymers in sequence to improve the clarification results at the lower concentration of the cationic polymer when the latter is used by itself.

This Example shows larger scale clarification. The fermentation broth was from production of an amino acid via a genetically modified strain of *E. coli*. Approximate level of bacterial cells was 6%. The appearance of the broth was an opaque, tan dispersion which settled on its own into 2 layers, each about 40% by volume in a settling period in the range from 8 to 10 hours. The pH of the broth was 2.5. The broth contained approximately 53 grams per liter of the amino acid. The object was to separate the dead bacterial cells from the supernate to facilitate the recovery of the amino acid in subsequent crystallization steps. The larger the flocs, the faster the settling time.

Two hundred and twenty-nine (229) gallons of broth was placed in a settling tank with a propeller-type mixer at 75 rpm. The broth was mixed with the anionic polymer for one (1) minute. A dosage of a high molecular weight and high charge density cationic derivative of polyacrylamide was then added to flocculate the suspension. Once the cationic polymer was then added it was mixed for 5 minutes and then the agitation was stopped. The percentage of settled cell material was measured after an additional sixty (60) minutes and the floc size was observed. The anionic polymer was added as a 10% dilution and the cationic polymer was added as a 0.3% dilution. The results are shown in Table 5.

TABLE 5

| Anionic additive | Conc. of anionic | Cationic additive | Conc. of cationic | Floc size | % settled after 60 minutes |
|---|---|---|---|---|---|
| None | 0 | Polymer 10 | 40 mg/L | small | 71.9% |
| Polymer 2 | 1000 mg/L | Polymer 10 | 20 mg/L | large | 78.1% |

EXAMPLE 6

Example 6 demonstrates the improved dewatering that can be achieved. A higher percent of solids in a cake were obtained when the sulfonated anionic polymer was used in the range of 500 to 1000 mg/L (or ppm) and the cationic polymer was used at 300 to 450 mg/L (or ppm).

This Example shows additional dewatering as in Example 3 using filter aids in addition to the anionic and cationic polymer to flocculate and settle a slurry of bacterial cells from a recombinant strain of *E. coli* used for the production of an amino acid. The concentration of cells in the slurry was 12% (w/w) with a pH of 2 to 3. The object of the test was to dewater the slurry as much as possible. The drier the sludge cake, the more effective the process.

To 500 mL of cell slurry in a one (1) liter beaker, was added filter aid (sodium bentonite clay or cellulose fibers) in an amount of 10,000 mg/L of broth, along with the anionic polymer and the slurry poured between two beakers for a total of 10 times. The cationic polymer was then added and poured back and forth for an additional 10 times. The resulting mixture was poured onto a belt of a vacuum filter, the belt travelling at approximately 1 foot per minute. Percent solids of the cake (if any) and the turbidity of the filtrate were observed and recorded. Anionic additives were added as a 5% solution and the cationic polymer was added as a 0.25% solution. The cationic polymer was a copolymer of acrylamide (20 mole %) and dimethylaminoethyl acrylate quaternized with methyl chloride. The molecular weight of the cationic polymer was approximately 5 million. The cationic polymer was a 32% active inverse-emulsion polymer. The results are shown in Table 6.

TABLE 6

| Anionic additive | Conc. of anionic | Conc. of cationic | Filter aid | Turbidity of filtrate | % Solids of cake |
|---|---|---|---|---|---|
| Control 1 | None | 300 mg/L | Clay | 400 NTU | 24.3% |
| Control 2 | None | 300 mg/L | Cellulose A | 770 NTU | 25.9% |
| Polymer 2 | 500 mg/L | 300 mg/L | Cellulose A | 400 NTU | 32.9% |
| Polymer 2 | 1000 mg/L | 300 mg/L | Cellulose A | 150 NTU | 31.9% |
| Polymer 2 | 500 mg/L | 450 mg/L | Cellulose A | 710 NTU | 33.4% |
| Polymer 2 | 1000 mg/L | 450 mg/L | Cellulose A | 760 NTU | 32.6% |
| Polymer 2 | 500 mg/L | 300 mg/L | Cellulose B | 725 NTU | 34.0% |
| Polymer 2 | 500 mg/L | 300 mg/L | Clay | 120 NTU | 31.1% |
| Polymer 2 | 1000 mg/L | 300 mg/L | Clay | 125 NTU | 26.6% |

Notes:
Polymer 2: Same as in Examples 3, 4, and 5.
Cellulose A: Cellulose fiber sold as Fibra-Cel SW-10, Cellite Corporation. 700 nm fiber length.
Cellulose B: Cellulose fiber sold as Fibra-Cel BH-40, Cellite Corporation. 200 micron fiber length.

Example 6 shows that the filter aids can benefit the method. Clay is cheaper; however, it does not burn if the disposal method contemplates incineration.

Most preferably the sodium alkyl sulfonate is used in an amount between 10 and 30 mole percent, the sodium acrylate in an amount of 15 to 70 percent and the balance is the acrylamide. Also, most preferably 70 to 90 mole percent of sodium acrylate is used with 10 to 30 mole percent of the sodium 2-acrylamido-2-methyl propane sulfonate.

While the present Examples are concerned with separation of dead cells from a solution containing the product, it is also contemplated that live cells can be separated for use in the various processes. The cells can be lyophilized or frozen after the separation as is well known to those skilled in the art.

It is intended that the foregoing description be only illustrative of the present invention and that the present invention be limited only by the hereinafter appended claims.

I claim:

1. A process for recovering a clarified broth by separating cells and parts thereof from an aqueous fermentation broth in which bacterial cells produce a water-soluble product, said process comprising, (a) sequentially mixing an anionic polymer ("Polymer A") and thereafter a cationic polymer ("Polymer C") in said broth wherein said cells are *Escherichia coli* ("*E. coli*"), said Polymer A has a viscosity in the range from 10 to 1 million cps at 15% by weight polymer solids in water alone, and said Polymer C has a viscosity in the range from 500 to 100,000 cps at 1% by weight polymer solids in water alone, so as to provide a concentration of polymers from 1 to 5000 parts per million in said broth, said Polymer A being a copolymer of first and second monomers, wherein said first monomer is selected from the group consisting of an $\alpha,\beta$-unsaturated monomer and an alkali metal or alkaline earth metal salt thereof, present in an amount from 5 to 95 mole percent, and said second monomer is selected from the group consisting of allyl sulfonic acid, methallyl sulfonic acid, allyl ether sulfonic acid, styrene sulfonic acid, methyl styrene sulfonic acid, vinyl sulfonic acid, 2-sulfoxy ethyl methacrylate, 2-acrylamido-2-methylpropane sulfonic acid, and a salt of each acid, wherein said salt is an alkali metal or alkaline earth metal salt, present in an amount in the range from 95 to 5 mole percent, said Polymer C being a polymer containing amine repeating units derived from an aminated $\alpha,\beta$-unsaturated monomer having a tertiary or quaternary alkyl amine group containing from 1 to 10 carbon atoms, wherein said aminated monomer is derived from said first monomer, wherein the ratio of Polymer A:Polymer C is in the range from 1:1 to 100:1 by weight;

(b) allowing a flocculant mass containing said Polymers A and C and said cells and parts thereof to separate from said broth; and, (c) removing said flocculant mass from said broth to produce a clarified broth.

2. The method of claim 1 wherein said broth has a pH in the range from 1 to 5.

3. The method of claim 2 wherein said first monomer is selected from the group consisting of sodium acrylate, maleic anhydride and acrylamide and said second monomer is selected from the group consisting of sulfonated styrene, 2-acrylamido- 2-methylpropane sulfonate and sodium allyl sulfonate.

4. The method of claim 2 wherein said Polymer C is a copolymer containing said amine repeating units and additional repeating units derived from said first monomer.

5. The method of claim 4 wherein said amine repeating units are derived from quaternized dimethylaminoethyl acrylate present in the range from about 10 to 99 mole percent, the remainder being acrylamide.

6. The method of claim 4 wherein said first monomer is selected from the group consisting of acrylamide and sodium acrylate and said second monomer is selected from the group consisting of sulfonated styrene and sodium 2-acrylamido-2-methylpropane sulfonate.

7. The method of claim 6 wherein said Polymer A is a copolymer of sodium acrylate and sodium 2-acrylamido-2-methylpropane sulfonate, said sodium acrylate being present in the range from about 70 to 90 mole percent, and said sodium 2-acrylamido-2-methylpropane sulfonate being present in the range from about 10 to 30 mole percent.

8. The method of claim 2 wherein said Polymer A has a Brookfield viscosity in the range from 6,500 cps to 50,000 cps at 15% solids.

9. The method of claim 2 wherein in step (a), additionally mixing a filter aid in said broth.

10. The method of claim 9 wherein said filter aid is selected from the group consisting of a clay and a cellulosic material.

11. The method of claim 1 wherein said broth has a pH in the range from 1 to 5, said *E. coli* produce an amino acid in said broth in which said *E. coli* are present in an amount in the range from and about 1 to 25 volume percent.

12. The method of claim 11 wherein said *E. coli* is a recombinant strain.

13. The method of claim 11 wherein said broth is at a pH in the range from 2 to 3.

14. The method of claim 1 wherein in step (a), additionally mixing a filter aid in said broth.

15. The method of claim 1 wherein said first monomer is selected from the group consisting of sodium acrylate, maleic anhydride and acrylamide and said second monomer is selected from the group consisting of sulfonated styrene, 2-acrylamido- 2-methylpropane sulfonate and sodium allyl sulfonate.

16. The method of claim 1 wherein said Polymer C is a copolymer containing said amine repeating units and additional repeating units derived from said first monomer.

17. The method of claim 1 wherein said Polymer A has a Brookfield viscosity in the range from 6,500 cps to 50,000 cps at 15% solids.

* * * * *